US011925709B2

(12) United States Patent
Johnson et al.

(10) Patent No.: US 11,925,709 B2
(45) Date of Patent: *Mar. 12, 2024

(54) TABLET FORMULATION FOR CGRP ACTIVE COMPOUNDS

(71) Applicant: Merck Sharp & Dohme Corp., Rahway, NJ (US)

(72) Inventors: Mary Ann Johnson, West Point, PA (US); Leonardo Resende Allain, Lansdale, PA (US); W. Mark Eickhoff, Lansdale, PA (US); Craig B. Ikeda, Harleysville, PA (US); Chad D. Brown, Quakertown, PA (US); Francis J. Flanagan, Jr., North Wales, PA (US); Rebecca Nofsinger, Lansdale, PA (US); Melanie Marota, Lansdale, PA (US); Lisa Lupton, South San Francisco, CA (US); Paresh B. Patel, Langhorne, PA (US); Hanmi Xi, Furlong, PA (US); Wei Xu, North Wales, PA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/110,398

(22) Filed: Dec. 3, 2020

(65) Prior Publication Data

US 2021/0085612 A1  Mar. 25, 2021

Related U.S. Application Data

(63) Continuation of application No. 16/178,641, filed on Nov. 2, 2018, now abandoned, which is a continuation of application No. 15/115,026, filed as application No. PCT/US2015/013672 on Jan. 30, 2015, now Pat. No. 10,117,836.

(60) Provisional application No. 62/087,366, filed on Dec. 4, 2014, provisional application No. 61/936,019, filed on Feb. 5, 2014.

(51) Int. Cl.
| A61K 9/20 | (2006.01) |
| A61K 31/437 | (2006.01) |
| A61K 31/4545 | (2006.01) |
| A61K 9/14 | (2006.01) |

(52) U.S. Cl.
CPC .......... *A61K 9/2077* (2013.01); *A61K 9/2009* (2013.01); *A61K 9/2013* (2013.01); *A61K 9/2027* (2013.01); *A61K 9/2031* (2013.01); *A61K 9/2054* (2013.01); *A61K 31/437* (2013.01); *A61K 31/4545* (2013.01); *A61K 9/146* (2013.01)

(58) Field of Classification Search
None
See application file for complete search history.

(56) References Cited

U.S. PATENT DOCUMENTS

| 4,166,452 A | 9/1979 | Generales, Jr. |
| 4,256,108 A | 3/1981 | Theeuwes |
| 4,265,874 A | 5/1981 | Bonsen et al. |
| 7,205,293 B2 | 4/2007 | Bell et al. |
| 7,390,798 B2 | 6/2008 | Williams et al. |
| 7,629,338 B2 | 12/2009 | Wood |
| 7,893,079 B2 | 2/2011 | Wood et al. |
| 8,481,556 B2 | 7/2013 | Bell et al. |
| 8,754,096 B2 | 6/2014 | Bell et al. |
| 8,883,807 B2 | 11/2014 | Bell et al. |

(Continued)

FOREIGN PATENT DOCUMENTS

| CN | 101018781 A | 8/2007 |
| CN | 101208303 A | 6/2008 |

(Continued)

OTHER PUBLICATIONS

Anonymous: "Handbook of Pharmaceuticals Excipients", 2000, Pharmaceutical Press, XP002773202, p. 386.

(Continued)

*Primary Examiner* — Leslie A. Royds Draper

(74) *Attorney, Agent, or Firm* — Foley Hoag LLP

(57) ABSTRACT

The present invention is directed to compositions comprising an extrudate or solid solution of a compound, or a salt thereof, of Formula I (API):

Formula I wherein "$R^a$" is independently —H or —F, in a water-soluble polymer matrix which further comprises a disintegration system allowing a tablet made therefrom to rapidly disintegrate in the environment in which the API is to be released.

10 Claims, 3 Drawing Sheets

(56) References Cited

U.S. PATENT DOCUMENTS

| | | |
|---|---|---|
| 8,895,572 B2 | 11/2014 | Burgey et al. |
| 8,912,210 B2 | 12/2014 | Bell et al. |
| 9,067,941 B2 | 6/2015 | Burgey et al. |
| 9,109,209 B2 | 8/2015 | Cabirol et al. |
| 9,174,989 B2 | 11/2015 | Chen et al. |
| 9,227,972 B2 | 1/2016 | Bell et al. |
| 9,227,973 B2 | 1/2016 | Bell et al. |
| 9,296,750 B2 | 3/2016 | Bell et al. |
| 9,376,431 B2 | 6/2016 | Xiang et al. |
| 9,409,916 B2 | 8/2016 | Bell et al. |
| 9,487,523 B2 | 11/2016 | Belyk et al. |
| 9,499,541 B2 | 11/2016 | Bell et al. |
| 9,499,545 B2 | 11/2016 | Bell et al. |
| 9,624,478 B2 | 4/2017 | Cabirol et al. |
| 9,833,448 B2 | 12/2017 | Bell et al. |
| 9,833,488 B2 | 12/2017 | Buyuktimkin et al. |
| 9,850,246 B2 | 12/2017 | Chen et al. |
| 10,106,541 B2 | 10/2018 | Chen et al. |
| 10,117,836 B2 | 11/2018 | Johnson et al. |
| 10,117,936 B2 | 11/2018 | Nebuloni et al. |
| 10,272,077 B2 | 4/2019 | Bell et al. |
| 2004/0076668 A1 | 4/2004 | Berchielli et al. |
| 2010/0179166 A1 | 7/2010 | Bell et al. |
| 2010/0227903 A1 | 9/2010 | Geers et al. |
| 2012/0122899 A1 | 5/2012 | Bell et al. |
| 2012/0122900 A1 | 5/2012 | Bell et al. |
| 2012/0122911 A1 | 5/2012 | Bell et al. |
| 2016/0051561 A1 | 2/2016 | Etter |
| 2016/0220552 A1 | 8/2016 | Mahjour et al. |
| 2016/0346214 A1 | 12/2016 | Johnson et al. |
| 2017/0189443 A1 | 7/2017 | Parsons |
| 2018/0008576 A1 | 1/2018 | Kleideiter et al. |
| 2018/0092899 A1 | 4/2018 | Liu et al. |
| 2018/0127417 A1 | 5/2018 | Chen et al. |
| 2019/0070161 A1 | 3/2019 | Mahjour et al. |
| 2019/0085061 A1 | 3/2019 | Burstein |
| 2019/0135927 A1 | 5/2019 | Levin |
| 2019/0209478 A1 | 7/2019 | Johnson et al. |
| 2019/0374518 A1 | 12/2019 | Trugman et al. |
| 2019/0374520 A1 | 12/2019 | Trugman et al. |
| 2020/0383983 A1 | 12/2020 | Brin et al. |
| 2021/0379029 A1 | 12/2021 | Trugman et al. |
| 2022/0031686 A1 | 2/2022 | Trugman et al. |
| 2022/0193051 A1 | 6/2022 | Trugman et al. |
| 2022/0340650 A1 | 10/2022 | Jakate et al. |
| 2023/0130736 A1 | 4/2023 | Boinpally et al. |

FOREIGN PATENT DOCUMENTS

| | | |
|---|---|---|
| CN | 101448821 B | 3/2013 |
| JP | 2008/512480 A | 4/2008 |
| JP | 2008/512481 A | 4/2008 |
| JP | 2010/529119 A | 8/2010 |
| JP | 2011/504481 A | 2/2011 |
| JP | 2012/528827 A | 11/2012 |
| KR | 10-2013-0087037 A | 8/2013 |
| RU | 2216317 C2 | 11/2003 |
| WO | WO-2004082602 A2 | 9/2004 |
| WO | WO-2004/092166 A2 | 10/2004 |
| WO | WO-2004/092168 A1 | 10/2004 |
| WO | WO-2006/031606 A2 | 3/2006 |
| WO | WO-2006/031610 A2 | 3/2006 |
| WO | 2006069754 A1 | 7/2006 |
| WO | WO-2007/092642 A2 | 8/2007 |
| WO | WO-2007/133491 A1 | 11/2007 |
| WO | WO-2008/153849 A1 | 12/2008 |
| WO | WO-2009/050234 A1 | 4/2009 |
| WO | WO-2009/065922 A2 | 5/2009 |
| WO | 2009100090 A1 | 8/2009 |
| WO | WO-2009/126530 A2 | 10/2009 |
| WO | 2010114801 A1 | 10/2010 |
| WO | WO-2010/139717 A1 | 12/2010 |
| WO | 2011156578 A1 | 12/2011 |
| WO | 2012064910 A1 | 5/2012 |
| WO | 2012121758 A1 | 9/2012 |
| WO | 2012122279 A1 | 9/2012 |
| WO | 2015038736 A2 | 3/2015 |
| WO | 2015119848 A1 | 8/2015 |
| WO | 2015120014 A1 | 8/2015 |
| WO | WO-2017/051385 A1 | 3/2017 |
| WO | WO-2019/050759 A1 | 3/2019 |
| WO | WO-2019/234709 A1 | 12/2019 |
| WO | WO-2019/234710 A1 | 12/2019 |
| WO | WO-2020/051137 A1 | 3/2020 |
| WO | WO-2020/214906 A1 | 10/2020 |
| WO | WO-2021/062282 A1 | 4/2021 |
| WO | WO-2022/140537 A1 | 6/2022 |
| WO | WO-2023/049920 A1 | 3/2023 |

OTHER PUBLICATIONS

Anonymous: "Handbook of Pharmaceutical Excipients", 2000, Pharmaceutical Press, XP002773225, p. 201.

Anonymous: "Remington, The Science and Practice of Pharmacy", 2000, Lippincott Williams & Wilkins, XP002773203, pp. 861-862.

Belikov V.G., "Pharmaceutical Chemistry," M. High School, (1993), 6 pages.

Cho et al., "Development of Novel Fast-Dissolving Tacrolimus Solid Disperson-Loaded Prolonged Release Tablet", European Journal of Pharmaceutical Sciences. Jan. 2014 [Online], 4:1-7. (Year: 2014).

Guo et al., "The Applications of Vitamin E TPGS in Drug Delivery," European journal of pharmaceutical sciences, (2013), 19(2), 175-186.

Holzer et al., "Evaluation of Sodium Stearyl Fumarate as a Tablet Lubricant," International Journl of Pharmaceutics, May 1979; 2(3-4): 145-153. (Abstract Only} (Year: 1979).

International Search Report and Written Opinion of the International Searching Authority in Application No. PCT/US15/13672 dated Jan. 30, 2015.

Pitt et al., "Determination of the Tensile Strength of Elogated Tablets," Powder Technology, 2013; 238:169-175, (2013).

Ramadhani et al., "Preparation and Characterisation of Kolliphor P188 and P 237 Solid Disperson Oral Tablets Containing the Poorly Water Soluble Drug Disulfiram", International Journal of Pharmaceutics. Sep. 2014 [Online], 475:514-522. (Year: 2014).

Anonymous "Sample Preparation of Pharmaceutical Dosage Forms", Springer, 2011, 5 pages.

Anonymous, "Handbook of Pharmaceutical Excipients", 5th Edition, Pharmaceutical Press, 2006, 10 pages.

Repka, et al., "Melt Extrusion: Process to Product", Expert Opinion on Drug Delivery, Dec. 6, 2011, 9 (1):105-125.

International Preliminary Report on Patentability for International Application No. PCT/US2015/013672 dated Aug. 9, 2016.

"Pharmacokinetics in Patients with Impaired Hepatic Function: Study Design, Data Analysis, and Impact on Dosing and Labeling," U.S. Food and Drug Administration (2003).

60th Annual Scientific Meeting, American Headache Society, 60th Annual Scientific Meeting American Headache Society, AHS 2018. San Francisco, CA, United States. Jun. 28-Jul. 1, 2018.

Allergan plc. (Nov. 5, 2015), "Allergan Outlines Open Science Model and Highlights Key Development Programs at R&D Day, Press Release." Retrieved from the Internet: http://www/multivu.com/players/English/7671931-allergan-r-d-day/, (Allergan plc, 2015), 5 pages.

American Headache Society (Jun. 9, 2016), Clinical Data Presented at American Headache Society Meeting Shows Promise of New Treatments for Migraine Prevention [Press Release]. Retrieved from the Internet: (https://americanheadachesociety.org/news/clinical-data-presented-at-american-headache-society-meeting-shows-promise-of-new-treatments-for-migraine-prevention/), 5 pages.

Anonymous: "Highlights of Prescribing Information: Qulipta", retrieved online via <https://www.rxabbvie.com/pdf/qulipta_pi.pdf> (2021).

Anonymous: "Highlights of Prescribing Information: Ubrelvy (ubrogepant) tablets," retrieved online via <https://www.rxabbvie.com/pdf/ubrelvY-P i.pdf> (2021).

(56) References Cited

OTHER PUBLICATIONS

Ansel C.H., et al., "Pharmaceutical Dosage Forms and Drug Delivery Systems", 7th Edition, Lippincott Williams & Wilkins, 1999, pp. 367-369.
Armstrong., "Biohaven hopes to give Allergan a headache," Evaluate Vantage, retrieved online <https://www.evaluate.com/vantage/articles/interviews/biohaven-hopes-give-allergan-headache>: 3 pages (2018).
Arulmozhi et al., "Migraine: Current concepts and emerging therapies", Vascular Pharmacology, 43: 176-187 (2005).
Ashina et al. "Plasma levels of calcitonin gene-related peptide in chronic tension-type headache," Neurology 55.9: 1335-1340. (2000).
Awawdeh et al. "Quantitative analysis of substance P, neurokinin A and calcitonin gene related peptide in pulp tissue from painful and healthy human teeth," International endodontic Journal 35.1 : 30-36 (2002).
Bagley C.L., et al., "Validating Migraine-Specific Quality of Life Questionnaire v2.1 in Episodic and Chronic Migraine," Headache, Mar. 2012; vol. 5 2(3): pp. 409-421.
Beer et al. "Systemic neuropeptide levels as predictive indicators for lethal outcome in patients with postoperative sepsis," Critical care medicine 30.8 : 1794-1798 (2002).
Bell et al., MEDI 20: Discovery of AGN-241689: A potent, orally-acting CGRP receptor antagonist for migraine prophylaxis, 253 American Chemical Society, Abstracts, p. 20 (Apr. 2-6, 2017) (Year: 2017).
Bellamy et al. "Salivary levels of CGRP and VIP in rhinosinusitis and migraine patients," Headache: The Journal of Head and Face Pain 46.1 : 24-33(2006).
Bennet et al. "Alleviation of mechanical and thermal allodynia by CGRP8-37 in a rodent model of chronic central pain," Pain 86.1-2 : 163-175 (2000).
Bigal M.E., et al., "Body mass index and episodic headaches: a population-based study," Archives of internal medicine, Oct. 2007, vol. 167 (18), pp. 1964-1970.
Bigal M.E., et al., "Obesity and migraine: a population study," Neurology, 2006, vol. 66(4), pp. 545-550.
Boinpally et al., "63rd Annual Scientific Meeting American Headache Society: Evaluation of the pharmacokinetic interaction and safety of atogepant coadministered with esomeprazole magnesium", Headache 61(S1): pp. 1-178 (2021).
Boinpally et al., "Single-Dose Pharmacokinetics and Safety of Atogepant in Adults With Hepatic Impairment: Results From an Open-Label, Phase 1 Trial," Clinical Pharmacology in Drug Development 10(7): pp. 726-733 (2021).
Boinpally et al., "Single-Dose Pharmacokinetics and Safety of Ubrogepant in Adults With Hepatic Impairment: Results From an Open-Label, Phase 1 Trial," Clinical Pharmacology in Drug Development, 0(0): 1-8 (2022).
Brauser, D., "Phase 3 Strive and Arise Trials Show Efficacy, Safety for Erenumab in Migraine Prevention," Medscape Medical News, 2017.
Burstein et al. "An association between migraine and cutaneous allodynia," Annals of neurology 47.5 614-624. (2000).
Cady et al. "Elevated saliva calcitonin gene-related peptide levels during acute migraine predict therapeutic response to rizatriptan," Headache: The Journal of Head and Face Pain 49.9: 1258-1266. (2009).
Cala M.L., et al., "The Activity Impairment in Migraine Diary (AIM-D): A novel migraine- specific patient-reported outcome measure to assess functioning based on activity impairment in episodic and chronic migraine patients", MTIS2018-005, Cephalalgia, 2018, vol. 38, pp. 1-115.
Chedid et al., "Hepatocellular Carcinoma: Diagnosis and Operative Management," ABCD Arq Bras Cir Dig 30(4): pp. 272-278 (2017).
Chen et al. "Menopausal flushes and calcitonin-gene-related peptide," The Lancet 342.8862 :p. 49.(1993).
Cheng et al. "The concentration of inhibitor which causes 50 percent inhibition (I) of an enzymatic reaction," Biochem. Pharmacol 22 : 3099-3108 (1973).

Clinical Trial NCT02828020: Efficacy, Safety, and Tolerability Study of Oral Ubrogepant in the Acute Treatment of Migraine (Achieve I), https://clinicaltrials.gov/ct2/history/NCT02828020?V_1=View#StudyPageTop (2016).
Clinical Trial NCT02848326: Efficacy, Safety, and Tolerability of Multiple Dosing Regimens of Oral Atogepant (AGN-241689) in Episodic Migraine Prevention, https://clinicaltrials.gov/ct2/show/NCT02848326 (2016).
Clinical Trial NCT02867709: Efficacy, Safety, and Tolerability of Oral Ubrogepant in the Acute Treatment of Migraine (Achieve II), https://clinicaltrials.gov/ct2/show/results/NCT02867709 (2016).
Clinical Trial NCT03700320: Study to Evaluate the Safety and Tolerability of Treatment With Atogepant 60 mg Daily for the Prevention of Migraine in Participants With Episodic Migraine, https://clinicaltrials.gov/ct2/show/NCT03700320 (2018).
Clinical Trial NCT03777059: 12-Week Placebo-controlled Study of Atogepant for the Preventive Treatment of Migraine in Participants With Episodic Migraine, https://www.clinicaltrials.gov/ct2/show/NCT03777059 (2018).
Connor et al., "Randomized, controlled trial of telcagepant for the acute treatment of migraine", Neurology, 2009, pp. 970-977, 73.
Dahlof CGH. "Infrequent or non-response to oral sumatriptan does not predict response to other triptans—review of four trials," Cephalagia, Feb. 2006, vol. 26 (2), pp. 98-106.
Delay-Goyet et al. "Relative involvement oi substance P and CGRP mechanisms in antidromic vasodilation in the rat skin," Acta physiologica scandinavica 146.4 : 537-538.(1992).
Do et al., "Therapeutic novelties in migraine: new drugs, new hope?," The Journal of Headache and Pain, 20: Article 37 pp. 1-13 (2019).
Doods "Development of CGRP antagonists for the treatment of migraine," Current opinion in investigational Drugs 2.9: 1261-1268. (2001).
Doods et al. "Pharmacological profile of BIBN4096BS, the first selective small molecule CGRP antaaonist," British Journal of Pharmacology 29.3 : 420-423. (2000).
Edvinsson et al. "Characterization of the effects of a non-peptide CGRP receptor antagonist in SK-N-MC cells and isolated human cerebral arteries," European journal of pharmacology 415. : 39-44. (2001).
Edvinsson et al. "Neuropeptides in migraine and cluster headache," Cephalalgia 14.5 : 320-327 (1994).
Edvinsson et al., "Basic mechanisms of migraine and its acute treatment", Pharmacology and Therapeutics, 136: 319-333 (2012).
Edvinsson L. et al., "Neuropeptides in Migraine and Cluster Headache Review Article", Cephalalgia, Oct. 14, 1994 (Oct. 14, 1994), pp. 320-327, XP055542226.
Escott et al. "Trigeminal ganglion stimulation increases facial skin blood flow in the rat: a major role for calcitonin gene-related peptide," Brain research 669.i : 93-99 (1995).
Evans et al. "The asymmetric synthesis of. alpha.-amino acids. Electrophilic azidation of chiralimide enolates, a practical approach to the syntheses of (R) and (S)-alpha azido carboxylic acids," Journal of the American Chemical Society 112.10 : 4011-4030. (1990).
Foster et al. "Calcitonin gene-related peptide is chemotactic for human T lymphocytes," Annals of the New York Academy of Sciences 657.1 : 397-404. (1992).
Friesen et al., "Hydroxypropyl Methylcellulose Acetate Succinate-Based Spray-Dried Dispersions: An Overview," Molecular Pharmaceutics, 5(6): 1003-1019 (2008).
Gelaye B., et al., "Body composition status and the risk of migraine: a meta-analysis," Neurology, May 2017, vol. 88 (19), pp. 1795-1804.
Gennaro Alfonso R., "Remington: The Science and Practice of Pharmacy", 2000, 20th edition, Table of Contents.
Global Health Metrics, "Global burden of 369 diseases and injuries in 204 countries and territories, 1990-2019: a systematic analysis for the Global Burden of Disease Study 2019", The Lancet, 396 (10258), pp. 1204-1222.
Goadsby et al. "Release of vasoactive peptides in the extracerebral circulation of humans and the cat during activation of the

(56) References Cited

OTHER PUBLICATIONS trigerninovascular system," Annals of Neurology: Official Journal of the American Neurological Association and the Child Neurology Society 23.2 : 193-196 (1988).
Goadsby et al. "Vasoactive peptide release in the extracerebral circulation of humans during migraine headache," Annals of Neurology: Official Journal of the American Neurological Association and the Child Neurology Society 28.2 183-187. (1990).
Goadsby et al., "Safety, tolerability, and efficacy of orally administered atogepant for the prevention of episodic migraine in adults: a double-blind, randomised phase 2b/3 trail" (2020).
Goadsby, "Bench to bedside advances in the 21st century for primary headache disorders: migraine treatments for migraine patients," Brain 139(10): pp. 2571-2577 (2016).
Goodman & Gilman's The Pharmacological Basis of Therapeutics, Joel G. Hardman et al., eds., McGraw-Hill Professional, 10th ed. 2001, Table of Contents.
Harmon et al. "Reaction of arylsulfonyl azides with N-methylindole," The Journal of Organic Chemistry, 38.1, 11-16 (1973).
Herzog et al. "CGRP receptors in the gerbil spiral modular artery mediate a sustained vasodilation via a transient cAMP-mediated Ca2+-decrease," The Journal of membrane biology 189.3, 225-236. (2002).
Ho et al., "Efficacy and Tolerability of MK-097 (telcagepant), a new oral antagonist of cacitonin gene-related peptide receptor, compared with zoimitriptan for acute migraine; a randomised, placebo-controlled parallel-treatment trial":, vol. 372,pp. 2115-2123, The Lancet, 2008, pp. 2115-2123, 372.
Ho et al., "Randomized Controlled trial of an oral CGRP receptor antagonist, MK-0974, in acute treatment of migraine", Neurology, Apr. 1, 20085; 70 (16): 1304-12.
Ho et al., "Randomized Controlled Trial of the CGRP receptor antagonist telcagepant for migraine prevention", Neurology, Sep. 9, 2014; 83(11): 958-66.
Ho et al., "Randomized controlled trial of the CGRP receptor antagonist telcagepant for prevention of headache in women with perimenstrual migraine", Cephalalgia, Feb. 2016;36(2): 148-61.
Hoffman et al. "Capsaicin-sensitive nerve fibers induce epithelial cell proliferation, inflammatory cell immigration and transforming growth factor-alpha expression in the rat colonic mucosa in vivo," Scandinavian Journal of Gastroenterology 37.4,414-422. (2002).
Holland P.R., and Goadsby P.J., "Targeted CGRP Small Molecule Antagonists for Acute Migraine Therapy," Neurotherapeutics, Apr. 2018, vol. 15 (2), pp. 304-312.
Holzer et al. "Job queues and wages," Title Quarterly Journal of Economics 106.3, 739-768. (1991).
International Preliminary Report on Patentability for Application No. PCT/US2021/043791 dated Nov. 18, 2021.
International Preliminary Report on Patentability for International Application No. PCT/IB2019/054780 dated Dec. 8, 2020.
International Preliminary Report on Patentability for International Application No. PCT/US2020/028666 dated Oct. 28, 2021.
International Search Report and Written Opinion for Application No. PCT/IB2019/054780, dated Oct. 28, 2019, 8 pages.
International Search Report and Written Opinion for Application No. PCT/IB2019/054781, dated Oct. 22, 2019, 10 pages.
International Search Report and Written Opinion for Application No. PCT/US2022/077061 dated Jan. 4, 2023.
International Search Report and Written Opinion for International Application No. PCT/US2020/028666 dated Aug. 28, 2020.
International Search Report and Written Opinion for International Application No. PCT/US2020/052891 dated Feb. 17, 2021.
International Search Report and Written Opinion for International Application No. PCT/US2021/064853 dated Mar. 18, 2022.
International Search Report with Written Opinion corresponding to International Patent Application No. PCT/US2011/060081, dated Dec. 19, 2011.
Jakate et al., "Effects of CYP3A4 and P-glycoprotein inhibition or induction on the pharmacokinetics of ubrogepant in healthy adults: Two phase 1, open-label, fixed-sequence, single-center, crossover trials," Cephalalgia Reports, 4: 1-10 (2021).
Johnson et al., "A pharmacogenomic evaluation of migraine therapy", Expert Opinion on Pharmacotherapy, 8: 1821-1835 (2007).
Kasarala G et al., "Standard Liver Tests," Clinical Liver Disease, Jul. 2016, vol. 8 (1), pp. 13-18.
Kopruszinski et al., "Prevention of stress- or nitric oxide donor-induced medication overuse headache by a calcitonin gene-related peptide antibody in rodents," Cephalalgia, 37(6): 560-570 (2017).
Kristoffersen E.S., et al., "Migraine, Obesity, and Body Fat Distribution—a Population- Based Study," The journal of headache and pain, Aug. 2020, vol. 21 (1), pp. 97.
Lance "Headache Pathogenesis: Monoarnines," Neuropeptides, Purines & Nitric Oxide 3-9 (1997).
Lars Edvinsson: "CGRP as the target of new migraine therapies—successful translation from bench to clinic", Nature Reviews, Apr. 24, 2018 (Apr. 24, 2018). XP055476796.
Lassen et al. "CGRP may play a causative role in migraine," Cephalalgia 22.1 (2002): 54-61.
Late-Breaking Abstracts: 60th Annual Scientific Meeting, American Headache Society, 60th Annual Scientific Meeting American Headache Society, AHS 2018. San Francisco, CA, United States. Jun. 28-Jul. 1, 2018.
Li et al. "Effect of CGRP receptor antagonist CGRP8-37 on nociceptive response, NOS expression and NO content in the dorsal horn of spinal cord during formalin-induced inflammatory pain in rats," Chinese Journal of Applied Physiology. 20(3): 291-295. (2004).
Lipton et al., (Postgraduate Medicine, Minneapolis (2001) 109: 1-6)(2001).
Lipton R.B, et al., "Impact of NSAID and Triptan Use on Developing Chronic Migraine: Results from the American Migraine Prevalence and Prevention (AMPP) Study, " Headache, Nov./Dec. 2013, vol. 53 (10), pp. 1548-1563.
Magellan RX Management, Ubrogepant (Ubrelvy™) New Drug Update; retrieved online <https://www.hhs.texas.gov/sites/default/files/documents/about-hhs/communications-events/meetings-events/dur/may-2020/may-2020-durb-agenda-item-5c.pdf>: 8 pages (2020).
May et al. "Intractable eye pain: indication for triotans," Cephalalgia 22.3, 195-196.(2002).
Menard et al. "A calcitonin gene-related peptide receptor antagonist prevents the development of tolerance to spinal morphine analgesia," Journal of Neuroscience 16. 7, 2342-2351 (1996).
Merck, B.I. and Co Inc Harleysville PA USA et al: "Discovery of AGN-241689: A potent, orally-acting CGRP receptor antagonist for migraine prophylaxis", Abstracts of Papers, ACS National Meeting & Exposition; 253rd National Meeting of the American-Chemical-Society (ACS) on Advanced Materials, Technologies, Systems, and Processes; San Francisco, CA, USA, Apr. 2-6, 2017. American Chemical Society, vol. 253. Apr. 2, 2017 (Apr. 2, 2017). p. 20. XP009516497.
Messali A.J., et al., "Treatment persistence and switching in triptan users: a systematic literature review," Headache, Jul.-Aug. 2014, vol. 54 (7), pp. 1120-1130.
Messina R., et al., "CGRP—A Target for Acute Therapy in Migraine: Clinical Data," Cephalalgia, An International Journal of Headache, 2019, vol. 39(3), pp. 420-427.
Molina et al. "Induction of Insulin Resistance in Vivo by Amylin and Calcitonin Gene—Related Peptide," Diabetes 39.2, 260-265 (1990).
National Center for Biotechnology Information ""*Homo sapiens* mRNA encoding RAMP1 ,"" GenBank Accession No. AJ001014, 2 pages, (2008).
National Center for Biotechnology Information "*Homo sapiens* (clone HSNME29) CGRP type 1 receptor mRNA, complete ends," GenBank Accession No. L76380,2 pages, (1996).
Negro A., et al., "CGRP Receptor Antagonists: An Expanding Drug Class for Acute Migraine?," Expert Opinion on Investigational Drugs, 2012, vol. 21(6), pp. 807-818.
Negro A., et al., "Serotonin receptor agonists in the acute treatment of migraine: a review on their therapeutic potential," Journal of Pain Research, Mar. 2018, vol. 11, pp. 515-526.

(56) References Cited

OTHER PUBLICATIONS

Neuschwander-Tetri B.A. et al., "The upper limits of normal for serum ALT levels reported by clinical laboratories depend on local reference populations," Arch Intern Med., Mar. 2004, vol. 168(6), pp. 663-666.
Olesen et al. "Calcitonin gene-related peptide receptor antagonist BIBN 4096 BS for the acute treatment of migraine," New England Journal of Medicine 350.11, 1104-1110. (2004).
Ornello R., et al., "Migraine and body mass index categories: a systematic review and meta-analysis of observational studies," The journal of headache and pain, Mar. 2015, vol. 16 (1), 14 pgs.
Peterlin B.L., et al., "Obesity and migraine: the effect of age, gender and adipose tissue distribution," Headache, Jan. 2010, vol. 50 (1), pp. 52-62.
Petersen et al. "BIBN4096BS Antagonizes Human a-calcitonin Gene Related Peptide-C35 induced Headache and Extracerebral Artery Dilatation," Clinical Pharmacology & Therapeutics 77.3 :202-213.(2005).
Remington J.P "Remington's Pharmaceutical Sciences," 17th Edition Edited by Alfonso R. Gennaro, Mack Publishing Co, Journal of Pharmaceutical Science, 1985, vol. 74 (10).
Rohrenbeck et al. "Upregulation of COX-2 and CGRP expression in resident cells of the C36 Borna disease virus-infected brain is dependent upon inflammation," Neurobiology of disease 6.1 : 15-34.(1999).
Rowe R.C., et al., "Handbook of Pharmaceutical Excipients," APhA Publications, 4th edition, 2003. pp. 1-6.
Russo., "CGRP-Based Migraine Therapeutics: How Might They Work, Why So Safe, and What Next?," ACS Pharmacology & Translational Science, 2(1): 2-8 (2019).
Salmon et al. "Altered neuroadaptation in opiate dependence and neurogenic inflammatory nociceotion in aCGRP-deficient mice," Nature neuroscience 4.4, : 357-358. (2001).
Saunders, B., "Allergan 2015 R&D Day", (Nov. 5, 2015), Powerpoint Presentation, slide 1-3 and 49-51. (Allergan plc, 2015).
Scher A.I., et al., "Factors associated with the onset and remission of chronic daily headache in a population-based study, " Pain, Nov. 2003, vol. 106 (1-2), pp. 81-89.
Schini-Kerth et al. "CGRP enhances induction of NO synthase in vascular smooth muscle C38 cells via a CAMP-dependent mechanism," American Journal of Physiology—Heart and Circulatory Physiology 267.6 : 2483-2490 (1994).
Schuster et al., "Calcitonin Gene-Related Peptide-Targeted Therapies for Migraine and Cluster Headache: A Review," Clinical Neuropharmacology, 40(4): 169-174 (2017).
Scott., "Ubrogepant: First Approval," Drugs, 80: 323-328 (2020).
Serrano D., et al., "Effects of Switching Acute Treatment on Disability in Migraine Patients Using Triptans," Headache, Oct. 2013, vol. 53 (9), pp. 1415-1429.
Shaw et al., "Carprolactams as Potent CGRP Receptor Antagonists for the Treatment of Migraine", Bioorg Med. Chem Lett, 2007, pp. 4795-4798, 17.
Silberstein S.D., et al., "Pharmacologic treatment for episodic migraine prevention in adult," American Academy of Neurology, Apr. 2012, vol. 78 (17), pp. 1337-1345.
Spetz et al. "Momentary increase in plasma calcitonin gene-related peptide is involved in hot flashes in men treated with castration for carcinoma of the prostate," The Journal of urology 166.5, 1720-1723.(2001).
Szkutnik-Fiedler et al., "Pharmacokinetics, Pharmacodynamics and Drug-Drug Interactions of New Anti-Migraine Drugs-Lasmiditan, Gepants, and Calcitonin-Gene-Related Peptide (CGRP) Receptor Monoclonal Antibodies," Pharmaceutics, 12(12): 1-22 (2020).
Tepper et al., "Erenumab in chronic migraine with medication overuse" Neurology, 92(20): e2309-2320 (2019).
Tepper et al., "Safety and efficacy of erenumab for preventive treatment of chronic migraine: a randomised, double-blind, placebo-controlled phase 2 trial," The Lancet Neurology, 16(6): 425-434 (2017).
Viana M., et al., "Triptan non-responders: do they exist and who are they?," Cephalalgia, Aug. 2013, vol. 33 (11 ), pp. 891-896.
Voss et al., "A phase IIb randomized, double-blind, placebo-controlled trial of ubrogepant for the acute treatment of migraine," Cephalalgia, 36(9): 887-898 (2016).
Walker et al. "Mice lacking the neuropeptide a-calcitonin gene-related peptide are protected against diet-induced obesity," Endocrinology 151.9 : 4257-4269. (2010).
Wallengren "Dual effects of CGRP-antagonist on allergic contact dermatitis in human skin." Contact dermatitis 43.3—137-143 (2000).
Williamson et al. "The CGRP Family: Calcitonin Gene-Related Peptide (CGRP), Amylin, and Adrenomedullin, Landes," Bioscience 245-247.(2000).
Williamson et al. "Sumatriptan inhibits neurogenic vasodilation of dural blood vessels in the anaesthetized rat-intravital microscope studies," Cephalalaia 17.4 : 525-531 (1997).
Winter A.C. "Body mass index, migraine, migraine frequency and migraine features in women," Cephalalgia, Feb. 2009, vol. 29(2), pp. 269-278.
Wu et al., "Regulatory perspectives of Type II prodrug development and time-dependent toxicity management: Nonclinical Pharm/Tox analysis and the role of comparative toxicology," Toxicology 236(1-2): pp. 1-6 (2007).
Yang M., et al., "Validation of the Headache Impact Test (HIT-6™) Across Episodic and Chronic Migraine," Cephalalgia, Feb. 2011; vol. 31(3), pp. 357-367.
Yu et al. "Effects of calcitonin gene-related peptide-(8-37) on withdrawal responses in rats with inflammation," European journal of pharmacology 347.2-3, 275-282. (1998).
Zhang et al. "Arthritic calcitonin/a calcitonin gene-related peptide knockout mice have reduced nociceptive hypersensitivity," Pain 89.2-3, : 265-273. (2001 ).
Zheng et al. "Severity of neurological signs and degree of inflammatory lesions in the brains of rats with Borna disease correlate with the induction of nitric oxide synthase," Journal of virology 67.10, 5786-5791. (1993).
Barbanti et al., "The role of anti-CGRP antibodies in the pathophysiology of primary headaches," Neurol Sci 38 (Suppl. 1): pp. S31-S35 (2017).
Deen et al. "Blocking CGRP in migraine patients—a review of pros and cons," The Journal of Headache and Pain 18(96): 9 pages (2017).
Written Opinion of the International Search Report for PCT/US2011/060081 dated Dec. 19, 2011.

TABLET FORMULATION FOR CGRP ACTIVE COMPOUNDS

CROSS-REFERENCE TO RELATED APPLICATIONS

This application is a continuation of U.S. patent application Ser. No. 16/178,641, filed Nov. 2, 2018, which is a continuation of U.S. patent application Ser. No. 15/115,026, filed Jul. 28, 2016 now U.S. Pat. No. 10,117,836, which is a U.S. National Phase application under 35 U.S.C. § 371 of PCT Application No. PCT/US2015/013672, filed Jan. 30, 2015, which application in turn claims the priority of U.S. Provisional Patent Application Ser. No. 61/936,019 filed Feb. 5, 2014 and U.S. Provisional Patent Application Ser. No. 62/087,366 filed Dec. 4, 2014, the entire contents of each of which are herein incorporated by reference in their entirety.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. Calcitonin gene-related peptide (CGRP) is a potent vasodilatory neurotransmitter believed to play a key role in migraine pathophysiology. The initial human clinical validation of the CGRP target was provided by Boehringer Ingelheim in 2003 with the report that an IV formulation comprising olcegepant was efficacious in the acute treatment of migraine and the mechanism was confirmed by a study using telcagepant (a CGRP antagonist) in an oral formulation.

Newly developed CGRP antagonist compounds are described in published international application, publication no. WO 2012/064910, which are based on the structure of Formula I:

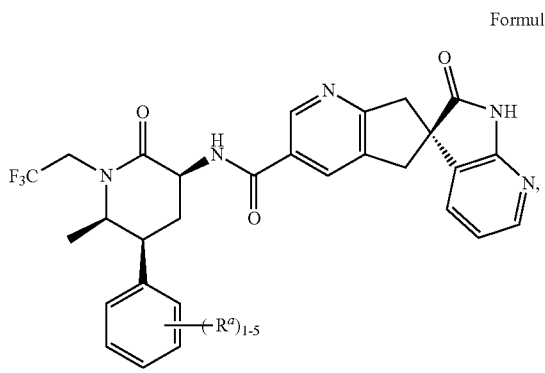

Formula I where "$R^a$" is various substituents (for example, where "$R^a$" is hydrogen: (S)—N-((3S,5S,6R)-6-methyl-2-oxo-5-phenyl-1-(2,2,2-trifluoroethyl)piperidin-3-yl)-2'-oxo-1',2',5,7-tetrahydrospiro[cyclopenta[b]pyridine-6,3'-pyrrolo[2,3-b]pyridine]-3-carboxamide and, for example, where three of "$R^a$" are selected to be fluorine: (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide). These compounds show promise as well-tolerated, potent CGRP-antagonist with low potential for side effects and metabolic complications. However, these compounds have low solubility and in general do not form salts suitable for the preparation of a stable pharmaceutical formulation.

For initial in vivo study it is common to administer poorly-soluble "class II" compounds formulated as a liquid formulation, for example, as a cosolvent or lipid-based solution employing a cosolvent such as PEG400, and other constituents as needed, to facilitate dissolution and enhance oral absorption. Although useful for clinical studies, in general it is not commercially attractive to provide a liquid formulation for oral delivery of medications for use in therapy for acute or chronic conditions or for use in prophylaxis treatment of chronic conditions. Desirably, such medicaments should be in a solid form for oral administration, for example, a pressed tablet or a capsule containing the API. In general, however, drugs with poor aqueous solubility are difficult to deliver in the gastrointestinal system without some solubility enhancer or permeation enhancer, or both, present at the site of absorption.

Solid dispersions, and, particularly, solid solutions, have been employed to promote the oral absorption of poorly water soluble active pharmaceutical ingredients (APIs), see, for example, Ford, Pharm Acta Helv, 1986, 61:69-88. Solid dispersions and solid solutions are compositions in which API is dispersed into or dissolved in a solid matrix, generally a polymer matrix. Solid solutions and solid dispersions (in which the active pharmaceutical ingredient forms a homogeneous or nearly homogeneous glass in the excipient matrix) are of particular interest in the oral delivery of poorly water soluble compounds. It is believed that these materials improve the absorption of orally administered API by improving: (i) the wetting properties of the API; (ii) causing at the point of absorption transient supersaturation of the API with respect to a lower energy (e.g. crystalline) phase API; or (iii) both effects. In general, solid solutions are believed to enable drug absorption by enhancing the dissolution rate and/or the extent to which the drug is dissolved from the matrix.

One example of a Class II drug which has been formulated as a solid solution is posaconazole, as described in International Patent Application, publication no. WO2009/129300, published Oct. 22, 2009. Such compositions of posaconazole were prepared by forming an extrudate of posaconazole in hydroxypropylmethylcellulose acetate-succinate-derivatized polymer (HPMC-AS), which solid dispersion was subsequently blended with microcrystalline cellulose, additional HPMC-AS, hydroxypropylcellulose, and magnesium sterate. This admixture was tableted to provide an orally bioavailable posaconazole formulation with desirable PK and bioavailability.

Another example of polymers employed in providing a solid solution of polymer and API is reported by Goertz et al. in U.S. Pat. No. 4,801,460 describes solid dispersions comprising a poorly soluble drug (exemplified by theophylline) and cross-linked polyvinylpyrrolidone/vinyl acetate copolymer (PVP copolymer). The '460 patent reports drug release times of up to 8 hours in tests, and does not discuss instant release medicaments employing such polymer matrix solid solutions.

In another example, in published international application publication no. WO98/029137 (the '137 publication), published Jul. 9, 1998, Takagi et al. describes compositions comprising an API dissolved in a matrix comprising a cellulosic polymer, for example, hydroxypropylmethyl-, hydroxyethyl- and hydroxypropyl-cellulose, and salts having an endothermic heat of dissolution, for example, sodium bicarbonate, which is said to improve the rate of disintegration. The '137 publication identifies the compositions taught therein as being similar to admixtures employing a carbonate or bicarbonate salt in the presence of a solid, water soluble acid which aids disintegration when exposed to an aqueous environment via effervescent action.

In another example, Fry et al. describe formulations of HER-2 inhibitors dispersed in a wide variety of polymer matricies, including many different derivatives of cellulosic polymers (including graft copolymers incorporating cellulosic moieties), polyvinyl alcohol polymers and polyvinylpyrrolidine polymers. See published international application publication no. WO2013/056108, published Apr. 18, 2013. Such compositions are said to reduce interpatient PK variability.

Despite their growing use, the design of solid solution formulations to effectively promote oral drug absorption remains largely a matter of trial and error. Successful formulation of lipophilic compounds as solid dispersions to promote oral absorption may benefit from a strong interaction between API and polymer. This has led to interest in partially water soluble polymers with amphiphilic properties like hydroxypropyl methylcellulose acetate succinate (HPMCAS), especially when the process used to create the solid dispersion is spray drying. See Friesen et al., Mol. Pharm., 2008, 5:1003-1019. While this approach was successful for many drug candidates, it was suggested that compounds with high melting points (or high ratios of melting point to glass transition temperature) and/or particularly lipophilic compounds (e.g., those with high log P values) are especially problematic to successfully formulate as solid solutions. Friesen et al. suggests that successful formulations of compounds having high melting point properties will likely be limited to relatively dilute concentrations of API in the solid dispersion.

As will be appreciated from the foregoing, while it is desirable to provide compounds of Formula I in the form of a solid for oral dosing administered via the GI tract, of necessity the nature of the therapy provided requires that the medicament make the compound of Formula I immediately available to the patient to whom it is being administered. There is a paucity of immediate release formulations reported at the present time based on solid dispersions or solutions of a class II API in a polymer matrix.

SUMMARY OF THE INVENTION

In one aspect the present invention provides a tablet comprising:
(a) an extrudate comprising:
    (i) a water-soluble polymer matrix;
    (ii) a dispersing agent; and
    (iii) a compound of Formula I, or a pharmaceutically acceptable salt thereof:

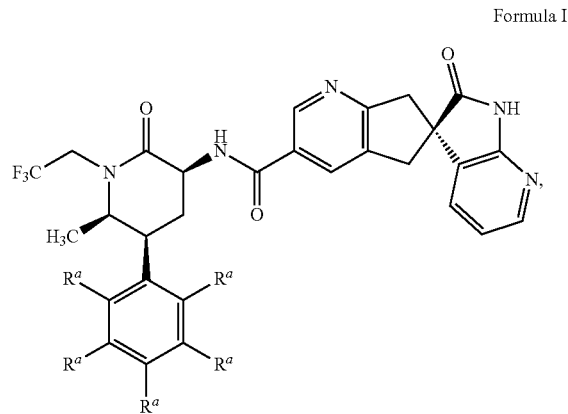

Formula I wherein "$R^a$" is independently —H or —F, and wherein the dispersing agent and compound of Formula I is dispersed within said polymer matrix; and
(b) a disintegration system,
wherein said tablet has a hardness of from about 12 kP to about 18 kP, and wherein said tablet achieves complete disintegration in less than about 5 minutes in a standard tablet disintegration test complying with USP 31-NF26 Chapt. 701 using aqueous HCl (pH 1.8) at 37° C.

In some embodiments it is preferred for the water soluble polymer matrix of said extrudate to be a polyvinylpyrrolidone/vinyl acetate copolymer (PVP-VA) matrix.

In some embodiments it is preferred for the disintegration system to comprise powdered sodium chloride and croscarmellose sodium, and more preferably in a 1:1 wt. ratio.

In some embodiments it is preferred for a tablet to have a hardness of from about 12 kP to about 16 kP. In some embodiments it is preferred for the tablet to have a tensile strength of about 1.75 MPa.

In some embodiments it is preferred for a tablet of the invention to release at least about 90 wt % of the compound of Formula I contained therein when subjected to a dissolution test complying with USP 30 NF25 Chapt. 711, apparatus #2 equipped with USP 2 paddles, operated at 50 rpm, in 900 ml of simulated gastric fluid (pH 1.8) at 37° C.

In some embodiments, preferably the tablet comprises a disintegration system comprising:
(a) Powdered Sodium Chloride, wherein said sodium chloride is characterized by: (i) a $d_{50}$ value of less than about 210 microns; (ii) a $d_{10}$ value of less than about 50 microns; and (iii) a $d_{90}$ value of less than about 470 microns; and
(b) croscarmellose sodium,
wherein said Powdered Sodium Chloride and said croscarmellose sodium are present in a 1:1 weight ratio, and wherein the amount of extrudate present in the tablet is selected to provide from about 9 wt. % to about 10 wt. % of the compound of Formula I dispersed therein.

In some embodiments it is preferred for the disintegration system to comprise about 20 wt. % of the tablet. In some embodiments the tablet comprises about 50 wt. % extrudate In some embodiments, the tableting formulation of the invention comprises (i) the extrudate; (ii) the disintegration system; (iii) one or more diluents, in some embodiments it is preferred to select mannitol and microcrystalline cellulose as diluents; (iv) a glidant, in some embodiments it is preferred to use colloidal silica as a glidant; and (v), and one or more lubricants, in some embodiments it is preferred to use sodium stearyl fumarate as a lubricant.

In some embodiments it is preferred for the compound of Formula I to be a compound of Formula Ia, or a salt thereof:

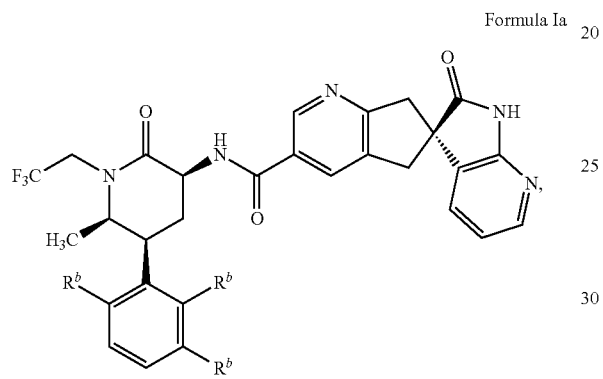

Formula Ia wherein, each of "$R^b$" is —H or each of "$R^b$" is —F.

In some embodiments, preferably the water-soluble polymer matrix of said extrudate is a water-soluble polyvinylpyrolidone/vinyl acetate copolymer, preferably a polyvinylpyrolidone/vinyl acetate copolymer made by free-radical polymerization of a 6:4 ratio of vinylpyrrolidone:vinyl acetate monomer.

In some embodiments where the compound of Formula I is a compound of Formula Ia, preferably, the compound of Formula a is present in the extrudate from about 20 wt % of the extrudated to about 22 wt. % of the extrudate.

In some embodiments, preferably the extrudate comprises α-tocepherol-polyethylene-glycolsuccinate (TPGS) as a dispersing agent, which is present in an amount comprising at least about 5 wt. % of the finished extrudate.

In some embodiments, preferably the extrudate comprises soluble polyvinylpyrolidone/vinyl acetate copolymer which is present in an amount comprising from about 50 wt. % of the extrudate to about 80 wt. % of the extrudate, preferably about 70 wt. % of the extrudate to about 75 wt. % of the extrudate.

In one aspect the invention provides a formulation suitable for providing a pressed tablet, the formulation comprising:

a) an extrudate composition comprising a water-soluble polyvinylpyrrolidone/vinyl acetate copolymer (PVP-VA copolymer) matrix and dispersed therein:

(i) an active compound of Formula Ia, or a pharmaceutically acceptable salt thereof:

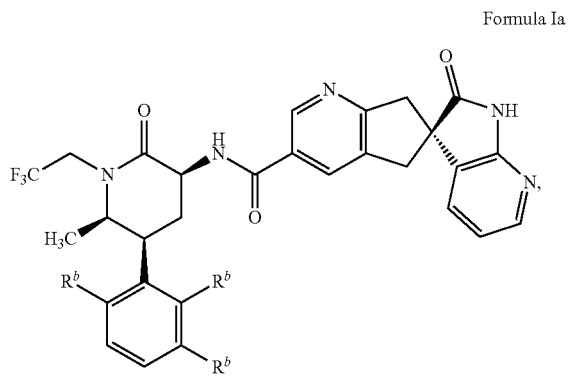

Formula Ia wherein all of $R^b$ are either —H or all of $R^b$ are —F; and (ii) tocepherol polyethylene glycol succinate (TPGS), wherein said compound of Formula Ia comprises from about 5 wt % to about 23 wt. % of said extrudate and TPGS comprises at least about 5 wt. % of said extrudate; and b) a disintegration system comprising: (i) croscarmellose sodium; and (ii) Powdered Sodium Chloride, wherein said disintegration system comprises about 20 wt. % of said formulation, and wherein said formulation is further characterized by providing a tablet having a hardness of from about 12 kP to about 18 kP, preferably about 12 kP to about 16 kP, which tablet when subjected to a dissolution test complying with USP 30 NF25 Chapt. 711, in a paddle-stirring apparatus equipped with USP 2 paddles, operated at 50 rpm, in 900 ml of simulated gastric fluid (pH 1.8) at 37° C. releases at least about 90% of the compound of Formula Ia contained therein in less than about 20 minutes.

In some embodiments a tablet formulation of the invention comprises in addition to extrudate and disintegration system: (i) mannitol, preferably about 20 wt. % of the formulation; (ii) microcrystalline cellulose, preferably up to about 20 wt. % of the formulation; (iii) colloidal silica, preferably about 0.25 wt. % of the formulation; and (iv) sodium stearyl fumarate, preferably about 0.75 wt. % of the formulation. In some embodiments, preferably the tablet formulation comprises about 50 wt. % of said extrudate.

DETAILED DESCRIPTION OF THE INVENTION

The following terminology, which may be used herein, is used in accordance with the following definitions.

Unless expressly stated to the contrary, all ranges cited herein are inclusive; i.e., the range includes the values for the upper and lower limits of the range as well as all values in between. As an example, temperature ranges, percentages, ranges of equivalents, and the like described herein include the upper and lower limits of the range and any value in the continuum there between.

The term "formulation", as used herein, refers to a blend, aggregation, solution or other combination of materials which includes an active pharmaceutical ingredient (API) which formulation is adapted to a particular mode of administration, for example, a formulation suitable for pressing into tablets designed for oral administration, in the treatment, management, prevention and etc. of a disease state or condition in a patient.

The term "subject" as used herein refers to an animal, preferably a mammal, most preferably a human, who has been the object of treatment, observation or experiment. When a human subject suffering from the condition to be treated is included in the activity they are alternatively referred to herein as a "patient".

As mentioned above, the present invention is directed to an extruded composition (extrudate) comprising a soluble polymer matrix and dispersed or dissolved therein a compound of Formula I, or a pharmaceutically acceptable salt thereof:

Formula I

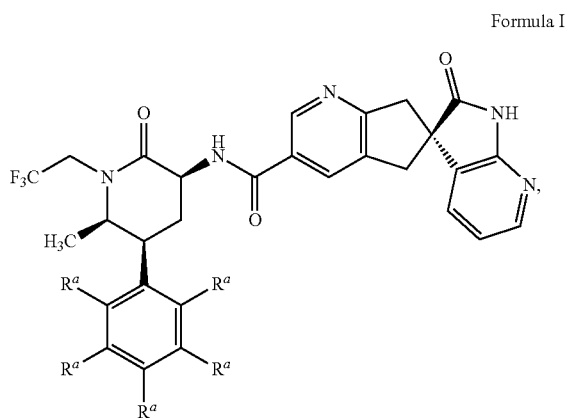

wherein "$R^a$" is independently —H or —F, and a dispersing agent, for example, vitamin E polyethylene glycol succinate (TPGS), which extrudate is incorporated into a pharmaceutical formulation comprising a disintegration system, which formulation is suitable for providing tablets of up to 18 kP, in some embodiments, preferably 16 kP, hardness which disintegrate within about 5 minutes in standard disintegration tests.

Compound of Formula I suitable for use in compositions of the invention may be prepared in accordance with the synthesis described in WO 2012/064910. In some embodiments it is preferable to crystallize the crude compound of Formula I prepared in accordance with the foregoing from an ethanol/water solvent, thus providing a crystalline trihydrate form of the compound, and to mill the crystalline material to a particle size that provides a free-flowing powder which can be fed into the extruder equipment used in preparing the dispersion. As will be appreciated, where noted, weights and weight percentage relationships described for the compound of Formula I in formulations and tablets described herein are adjusted to reflect the weight of an equivalent amount of 100% active free-base of the compound without solvent of crystallization or inert material as would be taken into consideration when preparing the formulation using materials having less than 100% activity.

Figure 1:
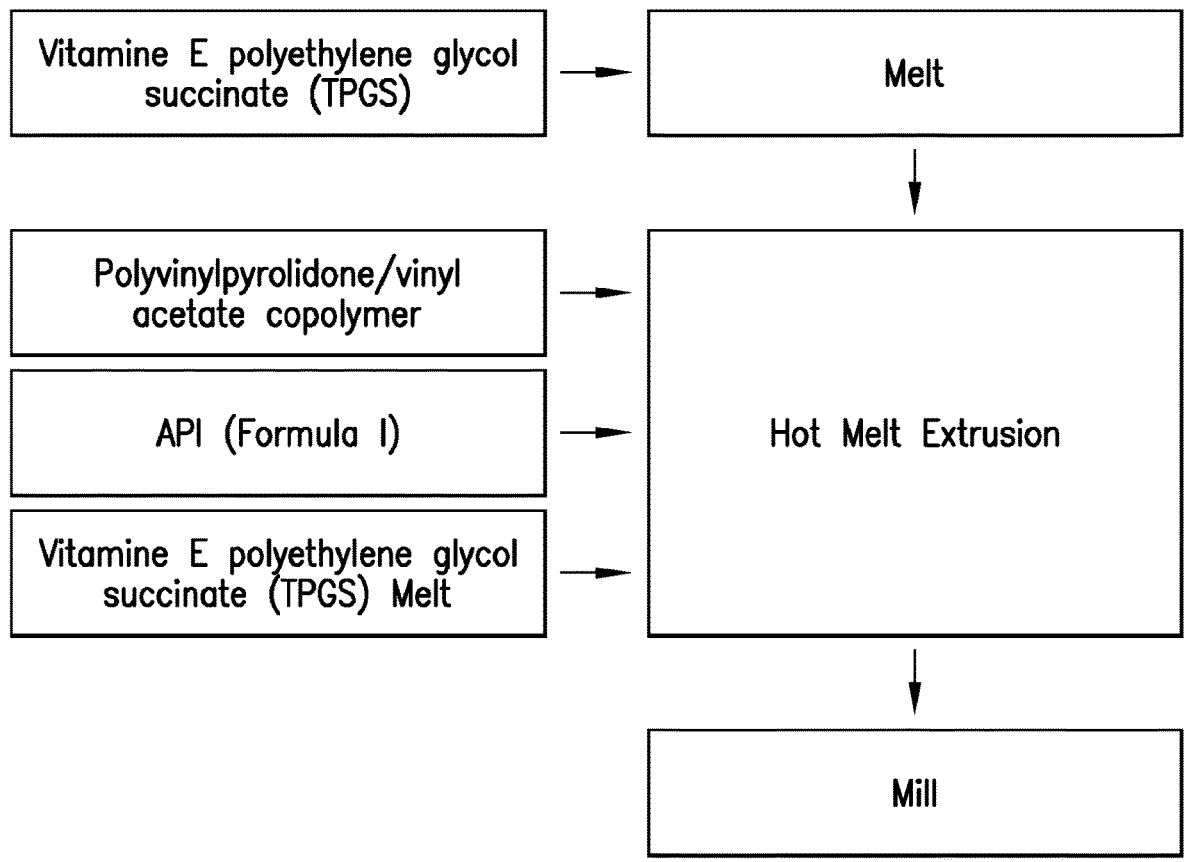
FIG. 1: Flow Chart Illustrating Unit Operations in General Prepartion of Dispersion of the Invention
Figure 2:
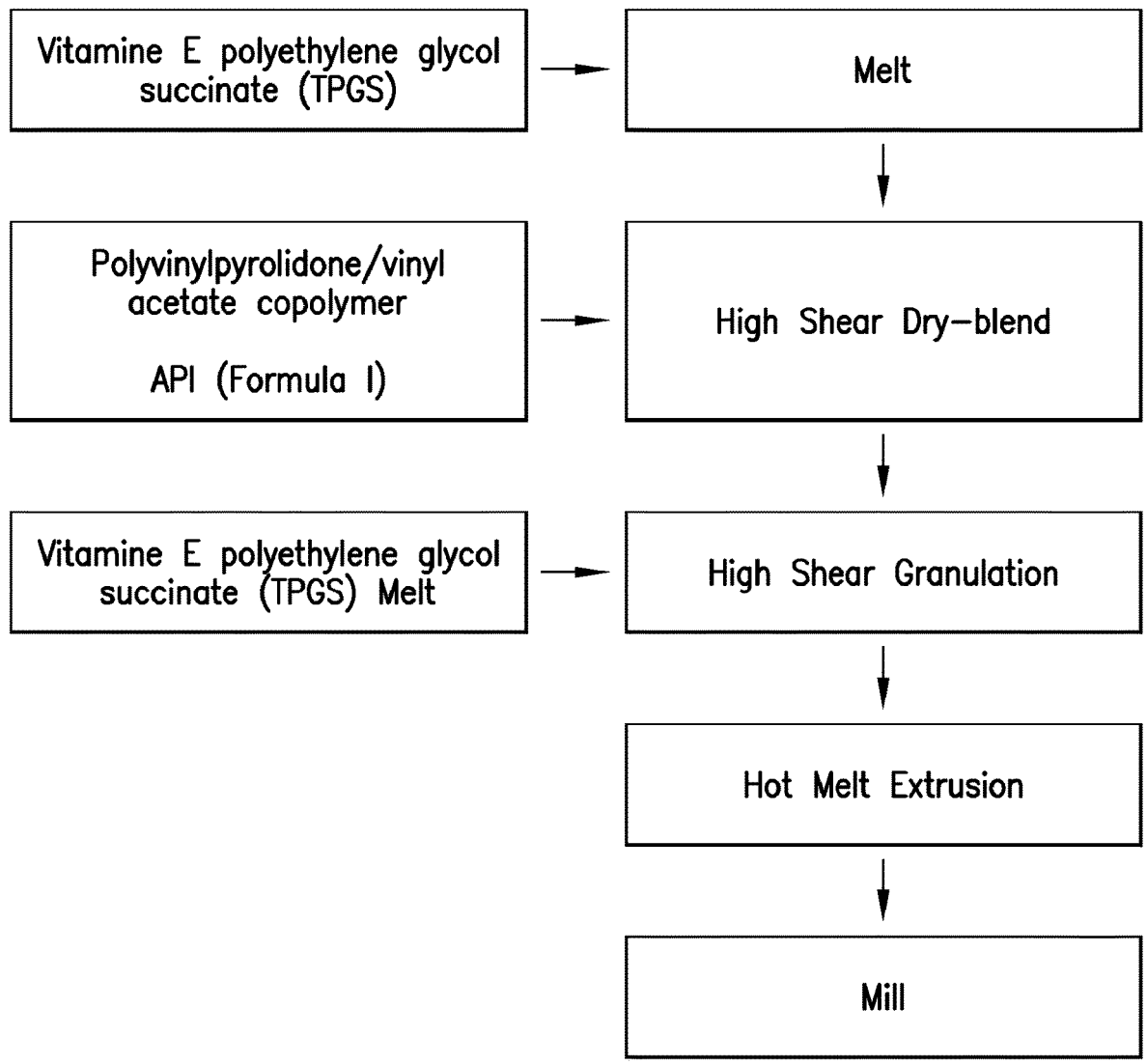
FIG. 2: Flow Chart Illustrating Unit Operations in Alternative General Prepartion of Dispersion of the Invention

With reference to FIGS. 1 and 2, in general the extrudate is prepared by hot-melt extrusion (HME) of a compound of Formula I and various excipients which may or may not have received additional operations to render them suitable for HME processing.

The inventors have surprisingly found that, contrary to common experience with Class II pharmaceutical compounds which are frequently dispersed in many different polymers, as discussed above, the compounds of Formula I tend to thermally degrade when attempts are made to incorporate them into a matrix comprising certain commercially available cellulosic polymers using HME techniques. For example, using HPMCAS as the polymer matrix leads to the formation of excessive degradation products in the dispersion produced. In some experiments, use of a cellulosic polymer as the dispersion matrix for preparing dispersions of the compound of Formula I by HME resulted in up to 25 times the amount of API degradation that subjecting the API alone to the same thermal excursion generated.

Surprisingly, the inventors have found that one type of commercially available polymer material from which a dispersion of the compound of Formula I could be prepared without exacerbating thermal degradation of the compound was the commercially available water-soluble polymers, for example, polyvinylpyrrolidone/vinylacetate copolymers (PVP-VA polymers). It was surprisingly found that dispersions prepared by HME technique using a water-soluble polymer, for example a PVP-VA polymer and a compound of Formula I resulted in no greater thermal degradation than subjecting the raw compound of Formula I alone to the same thermal excursion. Accordingly, intimate mixtures of free base compound "FIa-H" (the compound of Formula Ia wherein all of "$R^b$" are —H,) or of the free base compound "FIa-F" (the compound of Formula Ia wherein all of "$R^b$" are —F) and one of two potential matrix polymers were subjected to 2 minutes of heating to 170° C. on a TGA instrument stage, then cooled to room temperature and evaluated spectroscopically for the formation of known thermal degradation products. These data is summarized in Table I.

TABLE I

| Composition | Initial mole % degradation products present | 170° C., 2 min. Mole % degradation products present |
|---|---|---|
| FIa-H alone (crystalline material) | 0.18 | 0.18 |
| FIa-H alone (amorphous material) | 0.11 | 0.11 |
| FIa-F alone (amorphous material) | 0.11 | 0.11 |
| FIa-H + PVP-VA | 0.42 | 0.77 |
| FIa-H + HPMCAS | 0.15 | 3.57 |
| FIa-F + PVP-VA | 0.10 | 0.15 |
| FIa-F + HPMCAS | 0.08 | 2.25 |

As illustrated in Table I, these data indicate that some commercially available cellulosic polymers exacerbate thermal degradation of both the FIa-H compound and the FIa-F compound. Moreover, the inventors have found that typically HME processing temperatures can reach 180° C., which results in even greater percentage of loss of a compound of Formula I to degradation products. Thus, the investigators surprisingly found that dispersing compounds of Formula I in soluble copolymers of polyvinylpyrrolidone/ vinyl acetate copolymer (PVP-VA copolymer) using a hot-melt extrusion (HME) processing technique run with the same thermal excursions used when a cellulosic polymer was employed resulted in a reduction of degradation products detected in the extrudate product. Typically, the percentage increase of degradation product observed in such extrudate was no greater than the percentage of degradation product observed when samples of the same compound of Formula I was subjected to the same thermal excursion experienced in the IME process.

In accordance with the foregoing, suitable water-soluble polymers for use in compositions of the invention are any soluble PVP-VA copolymer which is made by free-radical polymerization of a 6:4 ratio of vinylpyrrolidone:vinyl acetate monomer. An example of commercially available copolymer of this type is the polyvinylpyrrolidone/vinylacetate copolymer sold under the trade name Kollidon® 64, and equivalents thereof.

In addition to a matrix polymer and at least one compound of Formula I, an extrudate of the invention will include some amount of an excipient which acts as a dispersing agent. As the term is used herein a dispersing agent can reduce the thermal energy required to drive compound of Formula I into solution in the matrix polymer and promote formation of the dispersion with even lower degradation losses in the compound of Formula I dispersed in the matrix. For extrudates of the invention, in some embodiments it is preferred to employ vitamin E in the form of its polyethylene glycol succinate (d-alpha-tocopheryl polyethyleneglycol succinate, or TPGS, herein). An example of a commercially available TPGS suitable for use in extrudates of the invention are any that provide esterified d-alpha-tocopheryl succinate with polyethylene glycol 1000, for example, but not limited to, Vitamin E d-α-TPGS NF from Eastman Chemical Company. In some embodiments, preferably TPGS is used as the dispersing agent and is present in the finished extrudate in an amount that is at least about 5 wt. % of the extruded composition.

It will be appreciated that other dispersing agents, for example, polyethoxylated castor oil (for example, cremophor) may also be employed.

The relative amount of the compound of Formula I, matrix polymer and dispersing agent employed in compositions of the invention, expressed as a wt. % of the extruded composition (extrudate), can vary and still be within the scope of the invention. Typically, the matrix polymer is present in an amount making up the balance of the composition after subtracting the wt. % of the API and dispersing agent. Typically the amount of matrix polymer is from about 70 wt. % to 75 wt. % of the finished extrudate. In some embodiments compositions of the invention are preferred that include an amount of the compound of Formula I which, corrected for its relative activity in comparison to 100% pure freebase compound of Formula I, is equivalent to no more than 25 wt. % of 100% free-base compound contained within the finished extrudate composition. In some embodiments, preferably the amount of the compound of Formula I present in the finished extrudate is equivalent in activity to from about 5 wt. % to about 22 wt. % of 100% pure free-base compound in the finished extrudate, and more preferably an amount equivalent in activity to at least about 20 wt. % of the 100% free base compound in the finished extrudate.

Compositions of the invention may be prepared by processes that are suitable for causing the selected API (for example, a compound of Formula Ia) to form a dispersion throughout the polymer matrix such that the drug is generally an amorphous uniform dispersion in the polymer or dissolved in the polymer. In general this requires some method of heating and mixing the constituents of the desired composition together and recovering the dispersion or solution in a solid form. Although it will be appreciated that any means affording a dispersion may be employed without departing from the invention, in some embodiments it is preferred to prepare compositions of the invention via Hot Melt Extrusion (HME). Hot melt extrusion (HME) is a technique in which an extruder, for example, a 27 mm Leistritz twin screw extruder, is employed to blend and heat the polymer, drug, and dispersing agent, whilst forming the finished composition dispersion or solution into a "noodle" or other conveniently handled shape which may be employed in further processing in the preparation of tableting formulations (extrudate).

In carrying out such operations, some or all of the components may be premixed prior to introducing them into the extruder, for example, by blending dry powders or wet milling or wet mixing, the constituents together in a blending, mixing or granulation process to insure intimately mixed constituents that lead to a homogeneous blend of constituents when the blend is fed into the extruder. Alternatively, the constituents may be fed into the extruder using independent feed streams (see Polymer Extrusion $4^{th}$ Edition by Chris Rauwendaal 2001, Hanser Gardner Publications, Inc., Cincinnati, OH or Schenck et al., (2010), Achieving a Hot Melt Extrusion Design Space for the Production of Solid Solutions, in Chemical Engineering in the Pharmaceutical Industry: R&D to Manufacturing (ed. D. J. am Ende), John Wiley & Sons, Inc., Hoboken, NJ, USA). Although for some compositions of the invention it is preferred to employ an HME process to prepare them, it will be appreciated that compositions of the invention can be prepared by any means useful for preparing a melt in any convenient apparatus in which an admixture of a compound of Formula I, matrix polymer and dispersing agent can be heated, mixed, and recovered.

In general, when extruding materials, the act of transporting the material through the extruder results in imparting energy to the material, which is converted to heat in the transported material. When heat transfer from the extruder power consumed in material transport is not by itself sufficient to achieve the temperature required to produce the desired dispersion or solution of a compound of Formula I in the polymer matrix, generally the barrel of the extruder is provided with means to impart additional heat to the material. In like manner, different sections of the extruder barrel can be heated or cooled, as needed, to maintain a particular temperature within a section of the extruder barrel or even extract heat in a different section of the extruder barrel to cool the material as it is passing through. In general the extruder temperature, power and transport speed of the extruder are set to provide the minimum temperature excursion and residence time needed to insure that a homogeneous dispersion or solution is prepared, thus minimizing the amount of API that undergoes degradation during processing.

In general, the extrudate emerging from an extruder is in a plastic state and solidifies upon emerging from the barrel due to pressure release and cooling. During this transition, typically the extrudate has a profile shape, for example, noodles, bars, cylinders, etc., and is "cut" into convenient length pieces. Once extrudate pieces are obtained, they can be further mechanically processed to provide a convenient form for incorporation into a dosage form, for example, by milling, grinding, or sieving. As the term is used herein, the material emerging from the extruder, and any form into which that material is subsequently rendered by mechanical processes, for example, milling, grinding, blending, sieving or granulating, is termed the "extrudate". Exemplary extruders include those provided by Leistritz, for example a 27 mm Leistritz twin screw extruder, and those provided by Thermo-Fisher, for example, a 16 mm twin screw Thermo-Fisher extruder. This equipment is generally equipped with means of heating the extruder barrel permitting it to be used in a "hot melt extrusion" operation.

Once the extrudate is rendered into a convenient form for further processing, it can be incorporated into a formulation for use in providing a dosage form suitable for oral administration, for example, a formulation adapted for pressing into tablets or filling into capsules. To achieve the dissolution and disintegration targets needed for effectively administering a compound of Formula I in the provision of migraine therapy, a formulation is prepared which comprises the finished extrudate, preferably milled to provide a powdered form that is easily blended with the other constituents of the formulation, a disintegration system and other excipients, for example diluent and lubricant, useful in preparing a formulation suitable for tableting. For use in a formulation of the present invention, the disintegration system comprises a conventional disintegrant, for example, croscarmellose sodium or crospovidone, and Powdered Sodium Chloride, where "Powdered Sodium Chloride" has the meaning presented herein.

For use in a disintegration system of the present invention, the phrase "Powdered Sodium Chloride" means sodium chloride which has been processed to a form having a particle distribution which yields the following values: (i) $d_{50}$ of less than about 210 microns, for example, about 195 microns; (ii) $d_{10}$ of less than about 50 microns, for example, between 43 microns and 44 microns; (iii) a $d_{90}$ of less than about 470 microns, for example, about 460 microns, and wherein the material displays a volume mean diameter of less than about 240 microns, for example, about 230 microns. An example of one such type of sodium chloride which is commercially available is provided by Avantor™ under the product designation "Sodium Chloride, Powder, USP GenAR® product no. 7540".

The data shown in Table II illustrate the need to employ Powdered Sodium Chloride in the disintegration system in formulations of the invention. Accordingly, test tablets comprising an extrudate of the invention (said extrudate comprising PVP-VA matrix, a compound of Formula Ia (FIa-H), and TPGS), a diluent comprising microcrystalline cellulose and a disintegration system consisting of crosscarmellose sodium and the salt shown in the left-hand column of Table II were subjected to a disintegration test complying with USP 31-NF26 Chapt. 701 in a standard disintegration testing apparatus (Pharamatron DT50) using aqueous HCl (pH 1.8) as a disintegration medium at 37° C. As reflected in Table II, surprisingly, only the tablet employing the Powdered Sodium Chloride in the disintegration system was able to meet the dissintegration target of less than 5 minutes (tablet compression force controlled to provide tablets of consistent hardness and thickness for all formulations).

TABLE II

| Salt in Disintegration System | Disintegration time, aqueous HCl (pH 1.8) |
| --- | --- |
| None | Greater than 1 hour |
| Powdered Sodium Chloride | 1.5 minutes |

TABLE II-continued

| Salt in Disintegration System | Disintegration time, aqueous HCl (pH 1.8) |
| --- | --- |
| Granular potassium carbonate | 6 minutes |
| Granular sodium chloride | 18 minutes |
| Granular sodium carbonate | 13 minutes |
| Powdered sodium bicarbonate | 17 minutes |
| Powdered sodium sulfate | 20 minutes |
| Granular sodium phosphate (dibasic) | 22 minutes |

Moreover, when equivalent tablets were made using Powdered Sodium Chloride alone, without croscarmellose sodium, it was found that tablet disintegration times exceeded 5 minutes as well. Accordingly, in some embodiments it is preferable that the disintegration system comprise a conventional disintegrant in conjunction with Powdered Sodium Chloride, and more preferably in a weight ratio of 1:1, Powdered Sodium Chloride:Disintegrant. Without being bound by theory, it is believed that the Powdered Sodium Chloride exhibits dissolution kinetics that are rapid compared with the rate of gelation of the polymer matrix when a tablet of the invention is exposed to the intended dissolution environment (human GI tract). Again without being bound by theory, the Powdered Sodium Chloride is believed by virtue of its particulate profile to have a combination of desirable dissolution kinetics and ability to form with sufficient rapidity (more rapidly than the rate of gelation of the matrix polymer) a local boundary layer of sufficient ionic strength to suppress gel-formation in the matrix polymer, and thereby to facilitate release of a compound of Formula I from the tableted formulation, which would otherwise be inhibited by gel formation in the matrix polymer. It will be appreciated that other salts if provided in a form which displays the same combination of rapid dissolution kinetics and the ability to rapidly form a local boundary layer of sufficient ionic strength to suppress gelation can also be employed in a formulation of the invention without departing from the scope of the invention defined herein.

In formulations of the invention, a suitable disintegrant for use in disintegration systems of the invention is, for example, croscarmellose sodium (crosslinked sodium carboxymethylcellulose polymer), for example, the AC-Di-Sol® line of polymers available from FMC. It will be appreciated that other disintegrants may be employed to provide an effective disintegration system, for example, crospovidone, if they are used in accordance with the other aspects of the disintegration system described herein and not depart from the scope of the invention.

The compounds of Formula I are directed to treatment of migraine, and as such, a rapid-release formulation is thought to be important in providing a therapeutic benefit to human patients to whom such a tablet is administered.

As is known, two qualities of tablet and capsule dosage forms important to release of an active pharmaceutical compound therefrom may be demonstrated using standard tests to measure the disintegration time and/or the dissolution time of the dosage form. A disintegration test measures the amount of time required for the dosage form to visibly disintegrate and wash out of a standard basket contained in a standard apparatus under standard operating conditions. A standard disintegration test is described for tablets and capsules in USP 31-NF26, Chapt. 701, beginning at p 266. There are equivalents thereto described in, for example, the European Pharmacopoeia and the Japanese Pharmacopoeia, which standard tests are generally accepted in the regulatory bodies of most countries. As the term is used herein with reference to formulations and tablets of the invention, "disintegration time" means: as determined in accordance with a test complying with this standard run at 37° C. using aqueous HCl (pH 1.8) as a disintegration fluid.

Dosage forms intended for oral administration may also be measured in a dissolution test, wherein the time-rate release of an amount of therapeutic compound dissolved into a standard media in a standard apparatus is measured after introducing the dosage form into the testing medium. A standard dissolution test for tablets and capsules is described in, for example, USP 36, chapt 711. Equivalent tests are described in the European Pharmacopoeia and the Japanese Pharmacopoeia, and in guidance from the US FDA, for example, in "*Guidance for Industry, Dissolution Testing of Immediate Release Solid Oral Dosage Forms*" published August, 1997 by the U.S. Department of Health and Human Services, Food and Drug Administration, Center for Drug Evaluation and Research, pp 1-13 and references therein. As the term is used herein with reference to formulations and tablets of the invention, "disintegration time" means: as determined in accordance with a test complying with this standard in a standard dissolution apparatus equipped with USP 2 paddles, operated at 50 rpm, in 900 ml of simulated gastric fluid (pH 1.8) at 37° C.]

In one aspect the invention provides a formulation adapted to preparing tablets comprising an extrudate of the invention, a disintegration system comprising Powdered Sodium Chloride and croscarmellose sodium, and other excipients, for example, diluents, glidants and lubricants, in amounts that, once the formulation is pressed into a table having a hardness of from about 12 kP to about 16 kP, and in some embodiments, 12 kP to about 18 kP, provides a tablet releasing more than 90% of the API contained therein in less than about 20 minutes when subjected to dissolution testing in a standard dissolution apparatus equipped with USP 2 paddles, operated at 50 rpm, in 900 ml of simulated gastric fluid (pH 1.8) at 37° C., in accordance with the procedures outlined in "*Guidance for Industry, Dissolution Testing of Immediate Release Solid Oral Dosage Forms*" published August, 1997 by the U.S. Department of Health and Human Services, Food and Drug Administration, Center for Drug Evaluation and Research, pp 1-13 and references therein where the tablet hardness exceeds.

Where tablet hardness is used herein, it is in reference to a tablet having a 500 mg target weight and a caplet shape or a 652.2 mg target weight in a caplet shape. Accordingly, as the term is used herein, tablets having a hardness in the range of 12 kPa to 16 kPa have a corresponding tensile strength of about 1.75 MPa, and tablets having a hardness in the range of 19 kPa to 22 kPa have a tensile strength of about 2.75 Mpa.

Formulations of the invention used in preparation of oral dosage forms (i.e., tablets or capsules) may further comprise other excipients. For example: a typical formulation of the invention directed to the preparation of a pressed tablet may contain a diluent (for example, mannitol, article of commerce, and/or microcrystalline cellulose, for example Avicel®); a glidant (for example, colloidal silica, for example Cab-O-Sil®); and a lubricant (for example, sodium stearyl fumarate, article of commerce). It will be appreciated that in formulating compositions of the invention, other diluents, glidants, and lubricants may be substituted to effect similar formulations.

The following definitions apply to excipients which may be used in formulations of the invention as the terms are used herein:

a diluent is an excipient which increase the bulk of a dosage form, typically where the active pharmaceutical ingredient in the formulation is too potent to permit convenient processing or administration of a dosage form which does not include a diluent, or where the formulation by itself without a diluent makes formation of the dosage form difficult (for example, where an aliquot of the formulation without a diluent would be of too small of a volume to form the aliquot into a tablet);

a disintegrant is an excipient that expands and/or dissolves when placed in an aqueous environment, for example, the gastrointestinal tract, which aids a tablet in breaking apart and promotes release of an active pharmaceutical ingredient contained in a tablet;

a "disintegration system" is a combination of a conventional disintegrant and a rapidly dissolving salt which provides beneficial antigellation effects when placed into an environment in which the dosage form within which the disintegration system is incorporated is placed into an environment in which the dosage form disintegrates, for example, simulate gastric fluid, the gastrointestinal tract of a subject or aqueous HCl at pH 1.8;

a Glidant is an excipient, for example colloidal silica, that enhances the flow of a granular mixture by reducing interparticle friction.

Pharmaceutical formulations intended for the preparation of oral dosage forms (tablets and capsules) may further contain one or more agents selected from the group consisting of sweetening agents, flavoring agents, coloring agents and preserving agents in order to provide pharmaceutically elegant and palatable preparations.

The preparation of formulations of the invention suitable for use in providing solid oral dosage forms comprising a composition of the invention may involve blending, roller compaction or wet granulation to densify and/or reduce the risk of segregation of components during subsequent handling (e.g., compression into tablets). Granulation steps can also be used to minimize the impact of raw material property variability (e.g., excipient particle size) on subsequent processing (e.g., tablet compression) and ultimate product performance. Lubrication is typically performed prior to roller compaction and tablet compression to reduce the tendency of material to adhere to compression surfaces (e.g., tablet tooling). In general lubricants are derivatives of stearic acid, for example, magnesium stearate or sodium stearly fumarate. Techniques and methods useful in preparation of dosage forms are know, for example, as described in Ansel, Introduction to Pharmaceutical Dosage Forms, Seventh Edition, 1999.

In general, preparation of oral dosage forms from pharmaceutical formulations of the invention requires that the pharmaceutical formulation of the invention (admixture of excipients, disintegrating system and composition of the invention) is compressed into a tablet or charged into a capsules. Tablets can be prepared with a variety of possible shapes (ellipsoidal, capsule, biconvex round, etc.). The powder can also be encapsulated in capsule dosage (e.g., using hard gelatin capsules). Techniques suitable for preparing solid oral dosage forms of the present invention are described in Remington's Pharmaceutical Sciences, 18th edition, edited by A. R. Gennaro, 1990, Chapter 89 and in Remington—The Science and Practice of Pharmacy, 21st edition, 2005, Chapter 45. In some embodiments of the present invention, it is preferred to prepare a tablet having a hardness of 16 kP or less, where the tablet has a target of providing the equivalent of 50 mg of a compound of Formula a (100% freebase), by placing 462.5 to 537.5 mg of the formulation into tableting tooling having an Elizabeth Carbide Die Company™ drawing number P-14305-B and pressing it in a Korsch™ tableting press.

Figure 3:
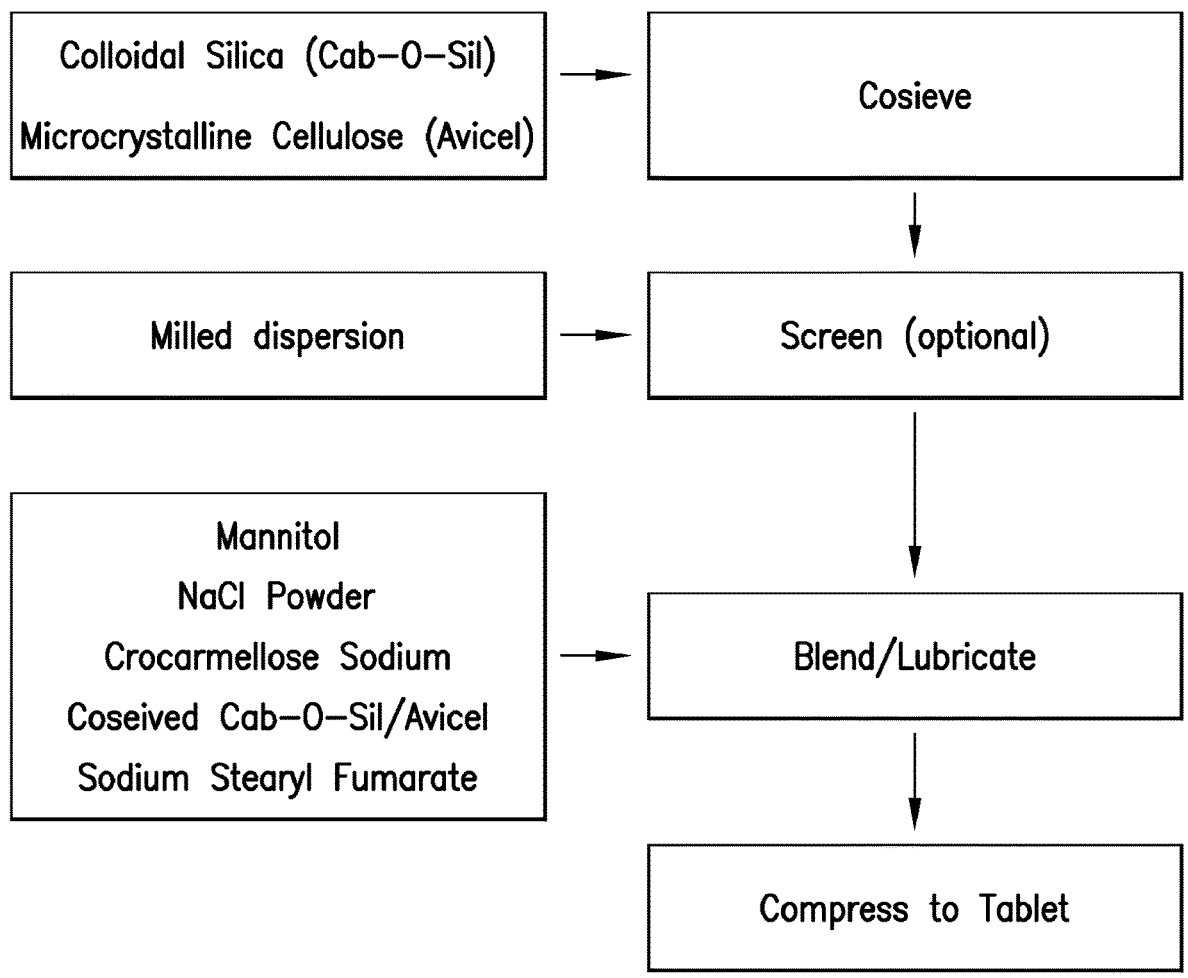
FIG. 3: Flow Chart Illustrating Unit Operations in Formulating Tablets of the Invention

With reference to FIG. 3, in general, compositions of the invention are prepared by dry-blending various excipients with milled dispersion (soluble polymer matrix comprising API dispersed therein), and compressing the blend to tablets.

What follows is a description of the general procedures employed in preparing the extrudate, preparing a tableting formulation comprising the extrudate and preparing tablets of the invention therefrom. The following examples serve only to illustrate the invention and its practice. The examples are not to be construed as limitations on the scope or spirit of the invention.

Example I—Preparation of a Extrudate Comprising Kollidon® 64, TPGS and (S)—N-((3S,5S,6R)-6-methyl-2-oxo-5-phenyl-1-(2,2,2-trifluoroethyl)piperidin-3-yl)-2'-oxo-1',2',5,7-tetrahydrospiro[cyclopenta[b]pyridine-6,3'-pyrrolo[2,3-b]pyridine]-3-carboxamide (FIa-H), a Tableting Formulation and Tablets Prepared Therefrom With reference to FIG. 2, extrudate comprising a water-soluble polymer matrix and dispersed therein API was prepared by:
  (i) forming FIa-H/Matrix polymer pre-mix by dry-blending an amount of crystalline FIa-H and polyvinylpyrolidone/vinyl acetate copolymer (Matrix polymer) to provide a pre-mix having a weight ratio of API:Matrix polymer of 1:3.75;
  (ii) feeding an amount of the API/Matrix pre-mix and an amount of molten alpha-tocopherol/propylene glycol succinate (TPGS) to provide a weight ratio of 19:1, API premix:TPGS into the extruder; and
  (iii) maintaining the extruder apparatus at a barrel temperature, feed rate and screw speed that provides an extrudate comprising a solid solution of the API in a matrix (polyvinylpyrrolidone-vinylacetate copolymer/TPGS) comprising about 20 wt % of the active API.

Accordingly, 1.318 Kg of FIa-H (compound of Formula Ia wherein all "$R^b$" are —H) tri-hyrdate was blended with 4.382 Kg of matrix polymer. TPGS (0.300 Kg) was melted and added to the blend of FIa-H and VA-64 in a high shear granulator. Blended API, VA-64, and TPGS was prepared in eight separate blending runs using a Diosna high shear granulator with a 6 L bowl, an impeller speed of 1000 rpm, a chopper speed of (600) rpm. In each run the blender was operated form 1 minute to mix FIa-H and the matrix polymer, then melted TPGS was added via pipette over 5 minutes of time maintaining the impeller and chopper speeds. After TPGS addition, the blend was mixed for an additional 1 minute maintaining the impeller and chopper speed.

The blend material was fed into a Thermo-Fischer 16 mm extruder while maintaining a product temperature of from about 146° C. to about 160° C., die pressure from about 14 bar to about 16 bar, a powder feed rate from 30-52 g/min., to provide 6.0 Kg of an extrudate of the invention. This material was milled in a Fitzmill equipped with screen size 0 (0.027") and using the following operating conditions: an impeller speed of 2000-4500 prm, and impact: forward blade direction. The milled extrudate material was sized by passing it through a 600 micron screen providing a powder (extrudate intermediate) having a VMD of approx 195 microns when measured by QICPIC for use in preparing a blend for pressing into tablets (tableting blend).

A tableting blend (6 kg) was prepared using 3.6 kg of extrudate intermediate comprising the equivalent of 200 mg/g of 100% freebase FIa-H, 1.160 kg of mannitol SD10, 0.600 kg of sodium choride powder, 0.600 kg of cross carmellose sodium, 0.01500 kg of colloidal silica, 0.09000 kg of sodium stearyl fumarate, and 0.5798 kg of Avicel PH102. The blender speed was 25 rpm and the blender time was 5 minutes.

The tableting blend was sub-divided to 1.250 kg sub-parts and tablets corresponding to hardness ranges of 12-16 kP, 19-22 kP, and 24-28 kP were prepared by compressing aliquots from each portion of the tableting blend on a Korsch XI100 equipped with upper and lower tools with face drawing P14305-B, that is a plain oval tool measuring 14.68 mm×8.33 mm.

Tablets having a hardness in the range of 12 kP to 16 kP were tested in accordance with a test complying with USP 30 NF25 Chapt. 711, paddle stirrer apparatus equipped with USP 2 paddles, operated at 50 rpm, in 900 ml of simulated gastric fluid (pH 1.8) at 37° C., these tablets met the release profile goal of 90% FIa-F contained in the tablet dissolved in less than 20 minutes.

Example II—Preparation of a Extrudate Comprising Kollidon® 64, TPGS and (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide) (FIa-F)), a Tableting Formulation and Tablets Prepared Therefrom Using the general preparation shown in Example I, 1.421 Kg of of FIa-F (compound of Formula Ia wherein all "$R^b$" are —F) was blended with 4.320 Kg of matrix polymer in a 25.0 L Fielder Granulator, impeller speed set to 'fast', chopper speed set to 'high'. Into the granulator was added 0.300 Kg of TPGS over five minutes while maintaining the impeller and chopper speeds. This blended material was hot-melt extruded in a Thermo-Fisher 16 mm extruder set to provide a product temperature of 158° C., powder feed rate of 20 g/minute, and die pressure maintained at 2-4 Bar, yielding 4.52 Kg of extrudate.

The extrudate thus prepared (3.3 Kg) was milled with a Fitzmill, screen size 000 (0.20"), with impact blade set in the 'forward' direction and an impeller speed set to target 3000 rpm (2000 rpm to 6000 rpm). Milled extrudate was screened through a 600 micron screen yielding 3.01 Kg of screened extrudate. A portion of the screened material (3.0 Kg) was blended with sodium stearyl fumarate (0.05625 Kg), silicon dioxide (0.01875 Kg), microcrystalline cellulose (0.9750 Kg), Powdered Sodium Chloride (0.750 Kg) and mannitol (1.950 Kg) using a V-blender operating at 24 rpm.

Two aliquots of the tableting blend prepared above (1.957 Kg) were pressed into tablets corresponding to hardness ranges of 12 kP-18 kP and 20 kP-26 kP respectively, on a Korsch XI100 tableting press equipped with upper and lower tools with face drawing P10165-B (plain/plain) oval tool measuring 15.88 mm×8.81 mm with a tablet target weight of 652.2 mg.

Tablets were dissolved in a paddle stir dissolution apparatus using simulated gastric fluid at 37° C., paddle speed 50 rpm in a test complying with USP 30 NF25 Chapt. 711, these tablets met the release profile goal of 90% of FIa-F contained in the tablet dissolved in less than 20 minutes, and the disintegration goal of complete disintegration in less than 5 minutes when tested using a disintegration test complying with USP 31-NF26 Chapt. 701 in a standard disintegration testing apparatus (Pharamatron DT50) using aqueous HCl (pH 1.8) as a disintegration medium at 37° C. tested in aqueous HCl (pH 1.8) at 37° C.

While the foregoing specification teaches the principles of the present invention, with examples provided for the purpose of illustration, the practice of the invention encompasses all of the usual variations, adaptations and/or modifications that come within the scope of the following claims.

The invention claimed is:

1. A tablet comprising:
   an extrudate comprising:
   a water-soluble polymer matrix;
   a dispersing agent; and
   a compound of Formula Ia, or a pharmaceutically acceptable salt thereof:

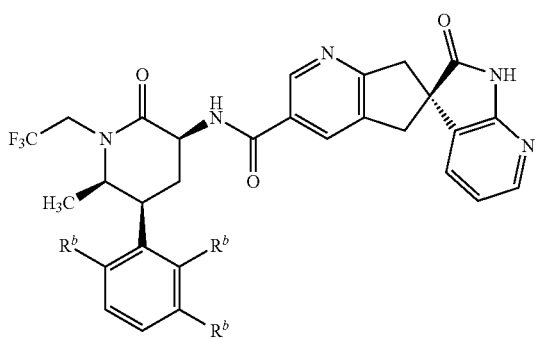

(Ia)

wherein each of $R^b$ is —H,
   wherein the compound of Formula Ia is dispersed within the polymer matrix; and
   a disintegration system.

2. The tablet according to claim 1, wherein the water-soluble polymer matrix is a water-soluble polyvinylpyrrolidone/vinyl acetate (PVP-VA) copolymer.

3. The tablet according to claim 1, wherein the disintegration system comprises a disintegrant selected from the group consisting of croscarmellose sodium and crospovidone.

4. The tablet according to claim 3, wherein the disintegrant is croscarmellose sodium.

5. The tablet according to claim 1, wherein the dispersing agent is selected from the group consisting of d-alpha tocopherol polyethyleneglycol succinate (TPGS) and polyethoxylated castor oil.

6. The tablet according to claim 5, wherein the dispersing agent is d-alpha tocopherol polyethyleneglycol succinate (TPGS).

7. The tablet according to claim 1, wherein the compound of Formula Ia is present in an amount from about 20 wt % to about 22 wt % of the extrudate.

8. The tablet according to claim 7, wherein the extrudate comprises about 50 wt % of the tablet.

9. The tablet according to claim 1, wherein the tablet has a hardness of from about 12 kP to about 18 kP.

10. The tablet of claim 1, wherein the disintegration system comprises powdered sodium chloride.

* * * * *